United States Patent [19]

Mueller et al.

[11] Patent Number: 5,053,044
[45] Date of Patent: Oct. 1, 1991

[54] CATHETER AND METHOD FOR MAKING INTRAVASCULAR INCISIONS

[75] Inventors: Richard L. Mueller, Mountain View, Calif.; Tommy G. Davis, Jacksonville, Tex.; Peter S. Brown, Los Altos Hills; John B. Simpson, Woodside, both of Calif.

[73] Assignee: Devices for Vascular Intervention, Inc., Redwood City, Calif.

[21] Appl. No.: 142,382

[22] Filed: Jan. 11, 1988

[51] Int. Cl.⁵ .............. A61M 25/00; A61B 17/32
[52] U.S. Cl. ............................ 606/159; 604/96; 606/170
[58] Field of Search ............... 604/22, 52, 53, 280, 604/96; 128/304, 305, 751–755, 344, 658, 898; 606/159, 170, 194

[56] References Cited

U.S. PATENT DOCUMENTS

| | | | |
|---|---|---|---|
| 3,704,711 | 12/1972 | Park | 128/305 |
| 4,273,128 | 6/1981 | Lary | 128/305 |
| 4,292,974 | 10/1981 | Fogarty et al. | 604/53 |
| 4,627,436 | 12/1986 | Lekrone . | |
| 4,685,458 | 8/1987 | Lekrone . | |
| 4,784,636 | 10/1988 | Rydell | 604/22 |

FOREIGN PATENT DOCUMENTS 0938977  6/1982  U.S.S.R. .............. 128/301

Primary Examiner—C. Fred Rosenbaum
Assistant Examiner—William Lewis
Attorney, Agent, or Firm—Townsend and Townsend

[57] ABSTRACT

A vascular catheter includes a blade tip at its distal end. In the specific embodiments, a blade is mounted within the blade tip and a mechanism provided for extending the blade transversely when the blade tip is located within a region of stenosis. By extending the blade and axially translating the catheter so that the blade forms an incision within the region of stenosis, improved angioplastic treatment can be achieved.

10 Claims, 4 Drawing Sheets

CATHETER AND METHOD FOR MAKING INTRAVASCULAR INCISIONS

BACKGROUND OF THE INVENTION

The present invention relates generally to the construction of catheters for angioplastic treatment of obstructed blood vessels, and more particularly to the construction and use of a novel catheter having a retractable blade at its distal end for forming incisions in atheromic plaque deposited within the blood vessels.

Balloon angioplasty was first described by Andreas Gruntzig in 1977. Dr. Gruntzig employed a balloon-tipped flexible catheter to percutaneously dilate a region of stenosis within the coronary artery of a patient with atherosclerotic coronary artery disease. Since the original work, the use of percutaneous balloon angioplasty has become widespread, with treatment of occluded peripheral blood vessels as well as coronary arteries.

Conventional balloon angioplasty relies on outward pressure from the balloon to compress the obstruction into the vessel wall. In successful treatment, the obstructing material remains compressed and unobstructed flow through the vessel is regained. In some cases, however, the atheromic material within the blood vessel has become hardened and calcified so that attempted dilation with a balloon causes cracking, tearing, and stretching of the blood vessel wall. In those cases, after the balloon catheter is removed, torn plaque and tissue can become dislodged from the vessel wall and cause abrupt reclosure of the vessel. Even when such abrupt reclosure does not occur, it appears that the irregular inner surface of the vessel wall (which results from the cracking and tearing) may contribute to restenosis at the same location within the vessel. In other cases, the plaque has so hardened that even with very high balloon pressures, successful dilation of the stenosed region is impossible.

For these reasons, it would be desirable to provide a method and apparatus for pretreating the region of stenosis to render the atheromic plaque more amenable to treatment by balloon angioplasty. It would be particularly desirable if such methods and apparatus greatly reduced or eliminated the incidence of restenosis after balloon dilation and allowed for successful balloon dilation in cases where the plaque would otherwise be refractory to such treatment.

SUMMARY OF THE INVENTION

According to the present invention, it has been found that the incidence of restenosis and abrupt reclosure previously associated with balloon angioplasty treatment of blood vessels can be greatly reduced by forming at least one axial incision within the atheromic plaque prior to dilation. The incision is made with a catheter having a blade located at its distal end. The blade is movable between a first position enclosed within the catheter and a second position extending from the catheter. By positioning the catheter within the blood vessel so that the distal end is proximate the obstruction, an incision may be formed by outwardly extending the blade and subsequently translating the catheter forward or backward to cut through the plaque in an axial direction. The process can be repeated to form multiple incisions. Alternatively, a catheter having two or more blades may be employed to achieve multiple incisions.

The construction of the catheter may vary greatly, and a number of specific catheter constructions are presented hereinafter. Conveniently, the blade may be pivotably mounted on a cylinder so that reciprocation of the cylinder causes the blade to engage a cam member which deflects the blade outward. Alternatively, the blade can be pivotally mounted on a fixed surface within the distal end of the catheter and actuated by a cable running from the proximate end of the catheter. Other modifications of the mechanical system employed to extend and retract the catheter blade would be obvious to one skilled in the art and are within the scope of the present invention.

DESCRIPTION OF THE SPECIFIC EMBODIMENTS

The present invention provides both apparatus and methods for angioplastic treatment of stenosed regions within blood vessels. Specifically, the present invention provides for the formation of one or more axial incisions within the atheroma of a stenosed region in order to improve the success rate of subsequent balloon angioplasty. The apparatus comprises a catheter having an extendible blade at its distal end. The method involves positioning the catheter so that the blade lies proximate the region of stenosis, extending the blade, and translating the catheter within the vessel so that the blade cuts axially through the atheroma. The procedure may be repeated to form more than one such axial incision, or the catheter may be provided with multiple blades so that more than one incision is formed with each passage of the catheter. The method may be performed as a standard pretreatment for subsequent angioplasty, or may be run only after attempted balloon angioplasty has proved unsuccessful.

Figure 1:
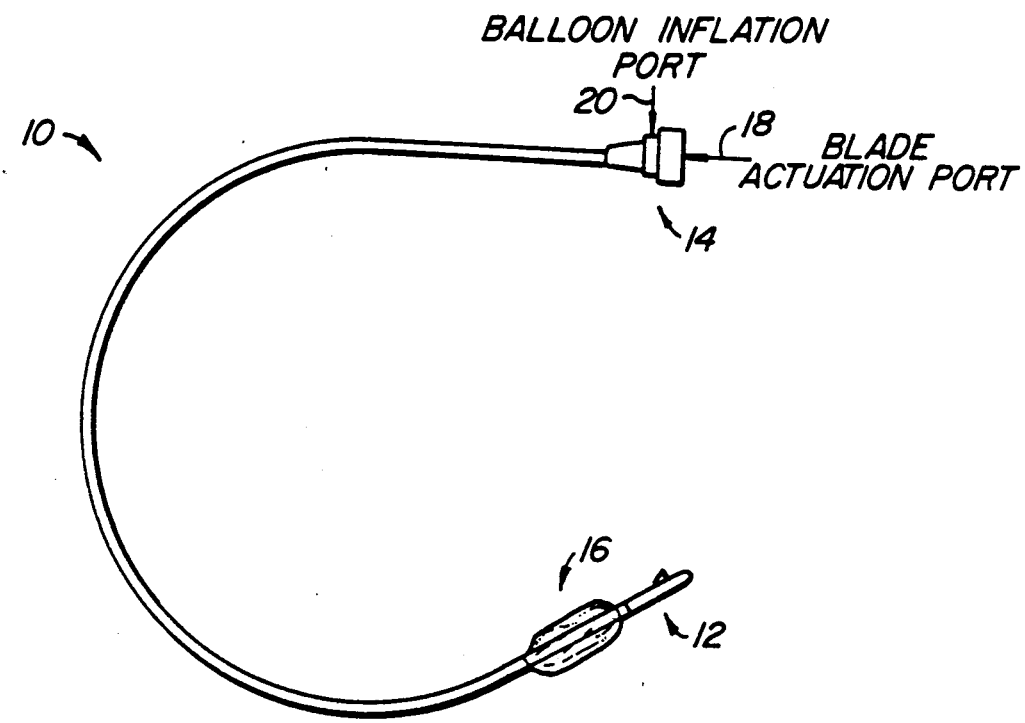
FIG. 1 illustrates a catheter constructed in accordance with the principles of the present invention.

Referring now to FIG. 1, a vascular catheter 10 constructed in accordance with the principles of the present invention includes a blade tip 12 at its distal end and a manifold connector 14 at its proximate end. Optionally, the catheter 10 includes a dilation balloon 16 at its distal end adjacent the blade tip 12. The manifold connector 14 includes a blade actuation port 18 and balloon inflation port 20 which are fluidly coupled to the blade tip 12 and dilation balloon 16, respectively.

The construction of vascular catheter 10 will be generally conventional, including an elongate flexible tube 22 (FIG. 2) which defines a lumen 24 and is the primary structural member connecting the manifold 14 and blade tip 12. Usually, at least a portion of the tube 22 will be radio-opaque or be clad with radio-opaque material to facilitate fluoroscopic tracking of the catheter 10. Suitable radio-opaque materials include barium and bismuth subcarbonate fillers for the flexible tube 22 and gold or platinum cladding materials. Balloon 16 may comprise a flexible sheath 26 formed over at least a portion of the tube 22. Specific methods for forming vascular catheters 10 suitable for use in the present invention are described in detail in co-pending applications Ser. No. 117,072, filed on Nov. 5, 1987, and Ser. No. 131,775, filed on Dec. 11, 1987, as well as U.S. Pat. No. 4,425,919, the disclosures of which are incorporated herein by reference.

The catheter constructions described in application Ser. No. 117,072 and U.S. Pat. No. 4,425,919, will generally be preferred as they are capable of transmitting torque from the proximate end of the flexible tube 22 to the blade-tip 12. Thus, by rotating the proximate end of tube 22, the blade tip 12 may be rotationally adjusted to properly align the tip within the region of stenosis.

Figure 2:
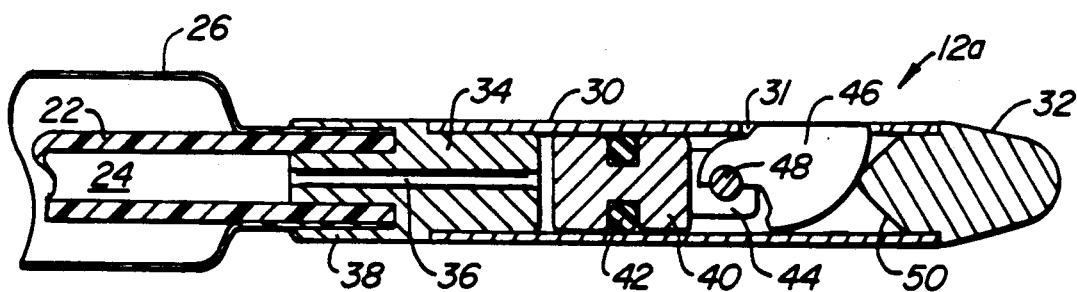
FIGS. 2, 3, and 3A are detail views of the catheter tip of a first embodiment of the present invention.
Figure 3:
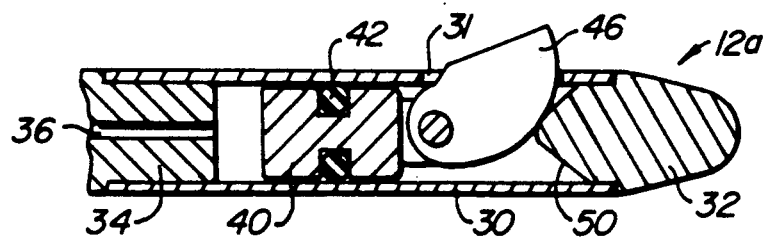

Referring now to FIGS. 2 and 3, a first embodiment 12a of the blade tip of the present invention will be described in detail. Blade tip 12a includes a cylindrical body 30 which is open at both ends. An end plug 32 seals the forward end of cylinders 30 and is generally rounded to facilitate introduction of the catheter into a desired blood vessel. Usually, the forward portion (to the right) of end plug 32 will be adapted to receive a guidewire (not illustrated) which is used in directing the catheter down the desired blood vessel. The rear end (to the left) of the cylinder body 30 receives a coupling member 34 which includes an axial passage 36 therethrough. The rear end of coupling member 34 receives the distal end of flexible tube 22, and the coupling member and flexible tube are sealed together by a clamping member 38. When sheath 26 is present, it will also be held in place by the clamping member 38.

Figure 3A:
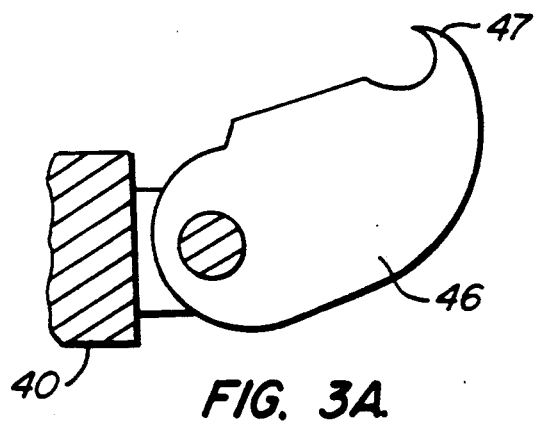

A piston 40 is received within the cylinder body 30 and is free to reciprocate therein. An O-ring 42 seals the piston 40 to the interior wall of the cylinder body 30. A clevis 44 is formed on the forward end of cylinder 40 and receives a blade 46 on pin 48 extending between the clevis members. The forward end of blade 46 engages a cam surface 50 formed on the rear portion of end plug 32. By moving the cylinder 40 forward, blade 46 is pushed against cam surface 50 and caused to deflect outward through slot 31 in cylinder 30, as illustrated in FIG. 3. Cylinder 42, of course, may be pushed forward by applying pressurized fluid through blade actuation port 18. The fluid will pass through lumen 24 and axial passage 36 to the rear surface of piston 40, causing the piston to move forward. Typically, a spring (not illustrated) will be provided to return the piston 40 to its retracted position as illustrated in FIG. 2. Alternatively, a vacuum (negative pressure) may be drawn through the lumen 24 to return the piston 40 to its retracted position. Also, the design of blade 46 may be modified as illustrated in FIG. 3A to provide a point 47 to facilitate initiation and continuation of the incision through the atheroma, as described in more detail hereinbelow.

The mechanism for extending the blade 46 of the present invention is not critical. In addition to the hydraulic actuation mechanisms illustrated herein, a variety of other mechanical and electromechanical schemes could be utilized. For example, a cable could be directed through the flexible tube 12 and connected to an eccentrically mounted blade in the tip 12. Force transmitted through the cable could then be used to extend the blade outward from the tip 12. Other modifications to the actuation mechanism could also be made. For example, double acting cylinders could be employed to positively extend and retract the blade, rather than relying on spring or vacuum retraction. In yet another variation on the blade activation design, the blade could be extended axially from the catheter, so that the catheter acts as a sheath protecting the blood vessel as the catheter is inserted. Once in place, the blade can be extended axially forward from the sheath so that it is exposed to form the incision within the atheroma A variety of other specific mechanisms for extending and exposing a blade within the interior of a blood vessel will occur to those skilled in the art.

Also, it will frequently be desirable to provide stops or constraints (not illustrated) which limit the extension of the blade to reduce the risk of perforating the blood vessel wall. The stops may be adjustable so that the blade extension can be varied depending on the size of the atheroma and blood vessel being treated.

Figure 4:
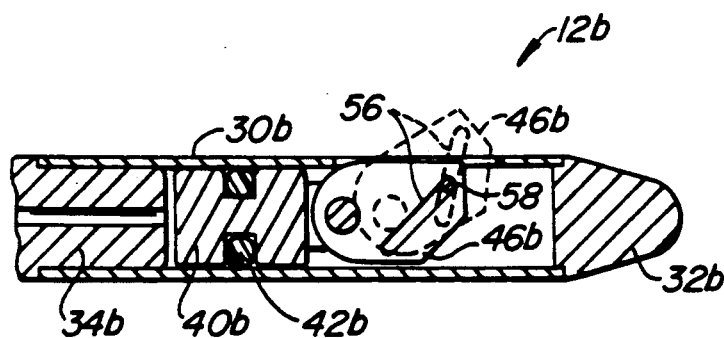
FIG. 4 is a detail view of the catheter tip of a second embodiment of the present invention, having a different cam mechanism for deflecting the blade.

Referring now to FIG. 4, an alternate embodiment of the blade actuation mechanism of the present invention will be described. Blade tip 12b includes cylinder body 30b and coupling member 34b. Piston 40b is mounted within the cylinder 30b, and includes O-ring 42b. The construction of the cylinder member 30b, coupling member 34b, piston 40b, and O-ring 42b, are all as described previously for the corresponding components of the first embodiment 12a described above. Blade 46b, however, differs from blade 46 in that it includes an oblique slot 56 formed therethrough. The slot 56 is received on a fixed pin member 58. The angle of the slot 56 is selected so that forward movement of the blade 46b causes the blade to deflect outward, as illustrated in broken line in FIG. 4. As the pin 58 acts as the cam, the end plug 32 does not need to include a rear cam surface as with the previous embodiment.

Figure 5:
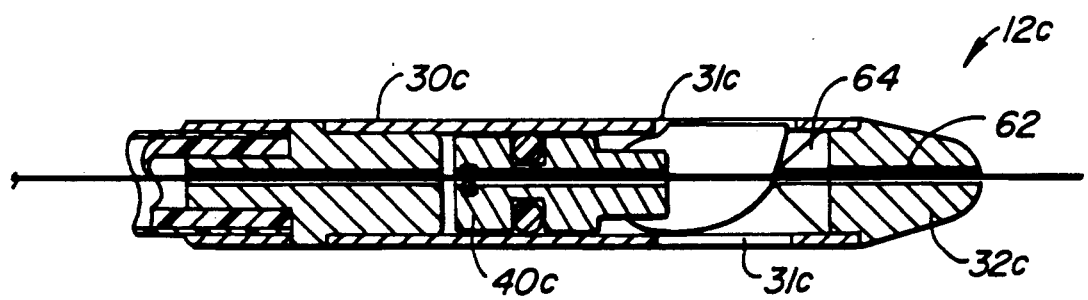
FIGS. 5 and 6 are detail views of the catheter tip of a third embodiment of the present invention, intended for insertion over a guidewire.
Figure 6:
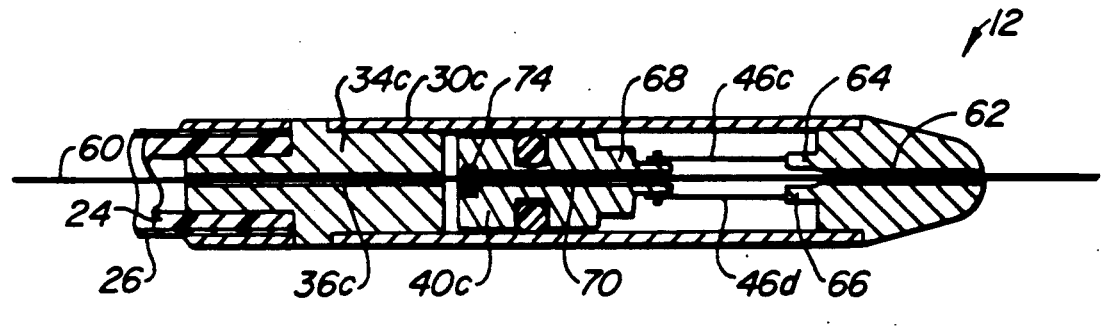

A second alternative embodiment of the present invention is illustrated in FIGS. 5 and 6, and is adapted to be positioned on a guiding wire 60. Additionally, the embodiment of FIGS. 5 and 6 is adapted to include a pair of transversely opposed blades 46c and 46d (best observed in FIG. 6). Cylinder member 30c is similar to cylinder member 30, except that it includes a pair of transversely opposed slots 31c. End plug 32c includes an axial passage 62 and a pair of rear cam surfaces 64 and 66, and the blades 46c and 46d are mounted on opposite sides of a mounting post 68 formed on the forward end of piston 40c. The piston 40c includes an axial passage 70 through its center, and axial passages 36c, 62, and 70, are generally aligned to allow passage of the guiding wire 60 therethrough. The axial passage 70 in piston 40c includes an O-ring 74 at its rear end to provide for sealing about the guiding wire 60. In this way, fluid pressure applied through the axial passage 36c in coupling member 30c acts against the piston 40c in a conventional manner. Forward motion of the piston causes both blades 46c and 46d to deflect outward from the cylinder 30c in opposed directions.

Figure 7:
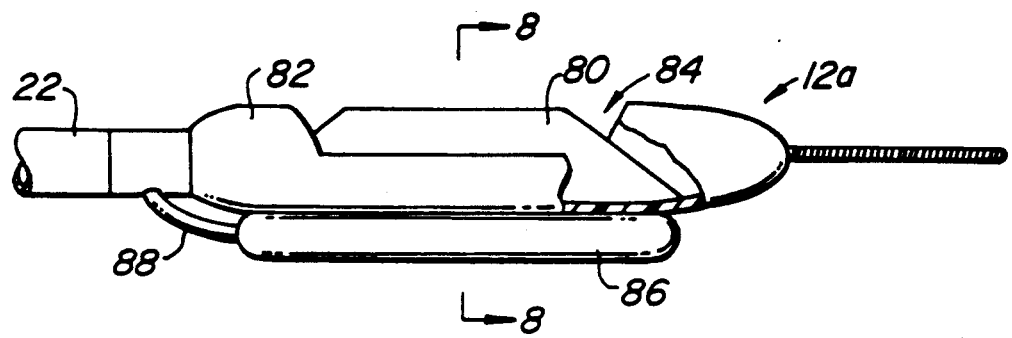
FIGS. 7 and 8 are detail views of the catheter tip of a fourth embodiment of the present invention, employing a fixed blade for making the incision.
Figure 8:
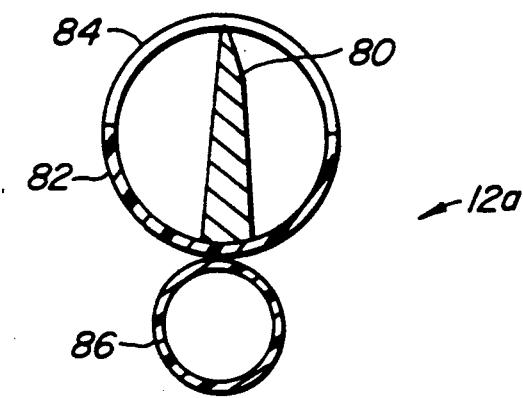

A third alternative embodiment of the present invention is illustrated in FIGS. 7 and 8, where blade tip 12a includes a fixed blade 80 mounted within tip enclosure 82. An opening 84 in tip enclosure 82 exposes the blade 80, and the blade may be urged in its cutting direction by balloon 86 mounted on the enclosure opposite to the blade. Balloon inflation media may be directed through a lumen (not illustrated) in flexible tube 22a. A connector conduit 88 can interconnect the balloon 86 and the lumen. A catheter having blade tip 12a operates by first positioning the blade tip so that blade 80 is oriented toward the desired region of the atheroma. By then inflating the balloon, the blade is strongly urged against the atheroma, and the catheter may be axially translated to form the desired incision.

Figure 9A:
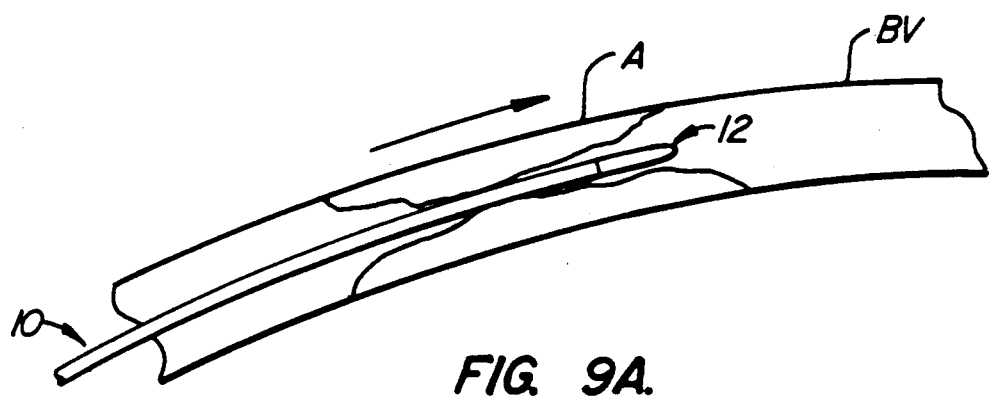
FIGS. 9A-9C illustrate the method of the present invention in treating a region of stenosis in a blood vessel.
Figure 9B:
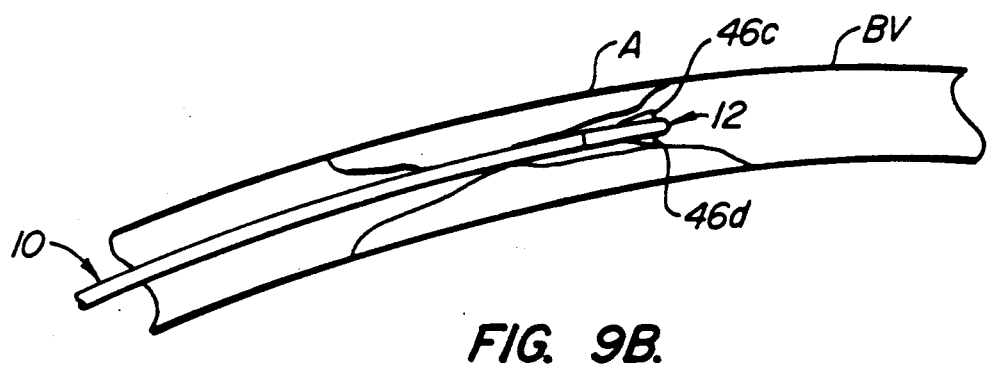
Figure 9C:
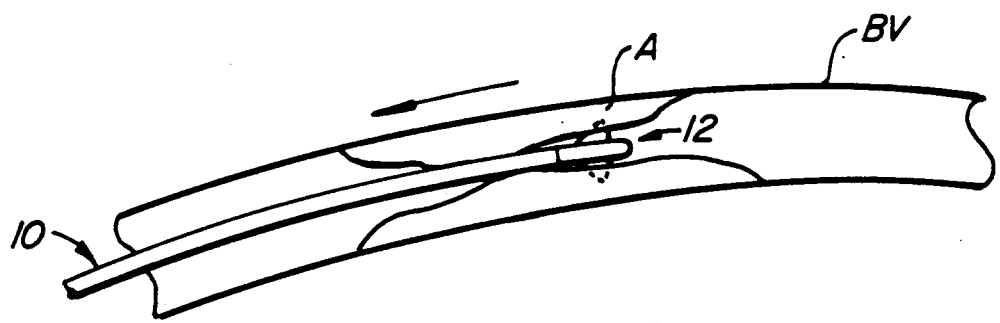

Referring now to FIGS. 9A-9C, use of the catheter 10 of the present invention in treating an atheroma A will be described. The atheroma A is present in a blood vessel, which may be a coronary artery or a peripheral blood vessel. The tip 12 of the catheter 10 will be positioned within the atheroma A, preferably so that the tip has passed through the restricted flow area within the atheroma. Catheter 10 is positioned by conventional means, typically under a fluoroscopic guidance. If desired, a guiding catheter may be first emplaced, and the guiding catheter used to guide the vascular catheter 10 according to conventional techniques.

Once in place, as illustrated in FIG. 9A, the blade tip 12 is extended radially outward by applying pressure through the blade actuation port 18 at the proximate end of catheter 10. Blades 46c and 46d are then extended transversely away from the tip 12, as illustrated in FIG. 9B. The catheter 10 is then drawn back through the atheroma A so that the blades 46c and 46d cut into the wall of the atheroma A, as illustrated in FIG. 9C. The procedure of FIGS. 9A-9C may be repeated one or more times in order to form a number of incisions.

After the incisions have been formed, balloon angioplasty can be carried out in a conventional manner. Specific methods for performing balloon angioplasty are well described in the patent and scientific literature and need not be described in detail herein. Conveniently, however, a dilation balloon can be formed as an integral part of the blade catheter of the present invention. With such a catheter, once the desired incisions have been formed, the blade(s) could be retracted and the balloon emplaced by simply translating the catheter. Balloon dilation could then be performed and the catheter removed after the entire treatment concluded.

Preferably, the activation force applied to blades 46c and 46d will initially be lower than that expected to be required for effective cutting. The blade will be axially translated followed by balloon dilation. The blade cutting may then be repeated with incrementally greater blade acuation force until satisfactory enlarging of the stenosed region is achieved. In this way, plaques having varying physical characteristics may be treated with a greatly reduced risk of perforation.

With catheters 10 having integral dilation balloons 16, it will frequently be desirable to inflate the balloon with low pressure, typically less than 20 psi during the incision procedure in order to stabilize the blade as it is drawn through the atheroma A.

Although the foregoing invention has been described in some detail by way of illustration and example for purposes of clarity of understanding, it will be obvious that certain changes and modifications may be practiced within the scope of the appended claims.

What is claimed is:

1. A catheter apparatus for forming incisions in the atheroma of a stenosed blood vessel, said catheter apparatus comprising:

an elongate catheter body having a proximate and a distal end;

a piston mounted to axially reciprocate within the distal end of the catheter body;

at least one blade pivotally mounted on the piston;

a cam member mounted to engage the blade as it is reciprocated by the piston and to shift the blade between a position projecting from the distal end; and means for reciprocating the piston.

2. A catheter apparatus as in claim 1, wherein the means for reciprocating the piston includes:

a lumen formed within the catheter body and extending from the piston to the proximate end; and means for supplying fluid under pressure to the piston through said lumen.

3. A catheter apparatus as in claim 1, wherein the cam member is a pin which engages a slot formed in the blade.

4. A catheter apparatus as in claim 1, wherein the cam member is a cam surface which engages the periphery of the blade.

5. A catheter apparatus as in claim 1, further comprising a pair of blades pivotally mounted on the piston and oriented to move in opposite directions when the piston is reciprocated.

6. A catheter apparatus for forming incisions in the atheroma of a stenosed blood vessel, said catheter apparatus comprising:

an elongate catheter body having a proximate and a distal end;

a housing secured to the distal end of the elongate catheter body;

a blade rigidly mounted to the housing, said blade being oriented radially so that it is able to form an axial incision when the catheter and housing are axially translated within a blood vessel; and a balloon positioned on the exterior of the housing at a location such that inflation of the balloon will urge the housing away from a vessel wall and move the rigid blade in a cutting direction.

7. A method for enlarging an atheroma within a blood vessel, said method employing a catheter having a balde at a distal end thereof, said method comprising:

positioning the catheter within the blood vessel so that the distal end lies substantially within the atheroma;

inflating a balloon mounted on a side of the distal end of the catheter opposite the blade so as to urge the blade into the atheroma;

axially translating the catheter blade to form an axial incision within the atheroma; and inflating a dilation balloon within the atheroma to expand the passage through the atheroma.

8. A method as in claim 7, wherein the dilation balloon is present on the same catheter as the catheter with the blade.

9. A method as in claim 7, wherein the dilation balloon is present on a different catheter than the catheter with the balde.

10. A method as in claim 7, wherein the blade is initially urged with a force less than that required to cut through the atheroma and wherein the force is thereafter incrementally increased.

* * * * *